(12) United States Patent
Katusic et al.

(10) Patent No.: US 7,235,298 B2
(45) Date of Patent: Jun. 26, 2007

(54) DOPED ZINC OXIDE POWDER, PROCESS FOR ITS PREPARATION, AND ITS USE

(75) Inventors: Stipan Katusic, Kelkheim (DE); Guenther Michael, Karlstein (DE); Peter Kress, Karlstein (DE); Guido Zimmermann, Hanau (DE); Andreas Gutsch, Ranstadt (DE); Geoffrey J. Varga, Freigericht (DE)

(73) Assignee: Degussa AG, Duesseldorf (DE)

( * ) Notice: Subject to any disclaimer, the term of this patent is extended or adjusted under 35 U.S.C. 154(b) by 109 days.

(21) Appl. No.: 10/522,778

(22) PCT Filed: Jul. 7, 2003

(86) PCT No.: PCT/EP03/07247

§ 371 (c)(1),
(2), (4) Date: Feb. 1, 2005

(87) PCT Pub. No.: WO2004/014800

PCT Pub. Date: Feb. 19, 2004

(65) Prior Publication Data

US 2006/0073092 A1   Apr. 6, 2006

(30) Foreign Application Priority Data

Aug. 5, 2002  (DE) ............................... 102 35 758

(51) Int. Cl.
  *B32B 5/66* (2006.01)
(52) U.S. Cl. ...................... 428/402; 428/403; 428/404; 428/405; 428/406

(58) Field of Classification Search ................ 428/402, 428/403, 404, 405, 406
See application file for complete search history.

(56) References Cited

FOREIGN PATENT DOCUMENTS

| EP | 0 597 380 | 5/1994 |
| EP | 0597380 A1 * | 5/1994 |
| GB | 435 005 | 9/1935 |
| WO | 03 080515 | 10/2003 |

OTHER PUBLICATIONS

Funahashi, Tsuneo. et al. "Manufacture of Zinc Oxide Fine Particles with Large Specific Surface Area", Chemical Abstracts+Indexes, vol. 109, No. 22, p. 167, XP000019653 1988.

* cited by examiner

*Primary Examiner*—Leszek Kiliman
(74) *Attorney, Agent, or Firm*—Oblon, Spivak, McClelland, Maier & Neustadt, P.C.

(57) ABSTRACT

Pyrogenically prepared, doped zinc oxide powder, wherein the doping component comprises at least one oxide from the group aluminum, gallium, indium, germanium, tin and is present in the doped zinc oxide powder in an amount of from 0.005 to 15 wt. %, and wherein the doped zinc oxide powder is in the form of aggregates of primary particles having a mean maximum diameter of from 30 to 400 nm. It is prepared by oxidation from zinc powder and at least one doping agent, wherein the process zones vaporisation, nucleation, oxidation and quenching are passed through and the doping agent is metered in in the nucleation zone, in which the temperature is below the boiling temperature of zinc. The doped zinc oxide powder can be used in electrically conductive lacquers and coatings.

20 Claims, 1 Drawing Sheet

DOPED ZINC OXIDE POWDER, PROCESS FOR ITS PREPARATION, AND ITS USE

Figure 1A:
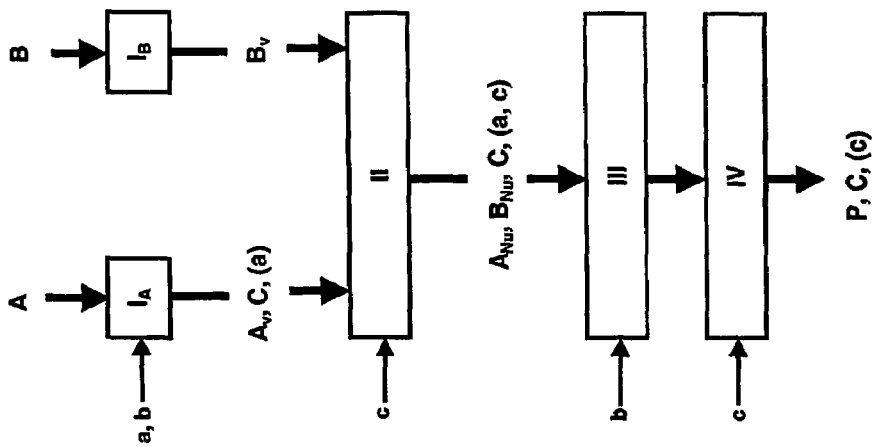

The invention relates to a doped zinc oxide powder, to its preparation and to its use.

Electrically conductive materials are required for many applications, such as, for example, in plastics, lacquers, coatings or fibres. In addition to electrical conductivity, it is in many cases desirable for such materials also to be largely transparent, for example in the case of pale or coloured coatings.

Examples of conductive materials are zinc oxides doped with oxides of the metals of the third or fourth main group.

It is known to prepare doped zinc oxides by coprecipitation from a solution of an alkali zincate and a doping agent by means of an acid (EP-A-404087, EP-A-405364).

It is also known to prepare doped zinc oxides by oxidation of a vapour mixture comprising zinc powder and a doping agent in an oxygen-containing atmosphere.

EP-A-598284 describes a process for the preparation of doped zinc oxide by oxidation of zinc vapour in the presence of doping agents selected from the group of the chlorides and bromides of aluminium, gallium, indium, tin, germanium or silicon. The doping agents are limited so that they must be free of oxygen atoms and their boiling points must not be higher than that of the zinc.

The known preparation processes usually yield needle-shaped or three-dimensionally branched, needle-shaped particles having sizes in the micrometer range. Such particles can have advantages over spherical particles in terms of electrical conductivity. However, their poor sintering behaviour and their poor dispersibility are disadvantageous.

Known spherical, doped zinc oxide particles are obtained by calcination of zinc oxide powder and gallium oxide in the presence of carbon in a reducing atmosphere (JP58-145620).

Similar processes are described in JP59-097531, JP58-145620 and U.S. Pat. No. 3,538,022. The disadvantage of the spherical particles prepared by those known processes is often their lower conductivity and lower transparency compared with the needle-shaped particles.

The object of the invention is to prepare an electrically conductive doped zinc oxide powder which has high transparency and does not have the disadvantages of the prior art.

The object is achieved by a pyrogenically prepared, doped zinc oxide powder, wherein the doping component comprises at least one oxide from the group comprising aluminium, gallium, indium, germanium, tin, silicon, which is characterised in that the doped zinc oxide powder is in the form of aggregates having a mean maximum diameter of from 30 to 400 nm and the doping component is present in an amount of from 0.005 to 15 wt. %.

Pyrogenically is to be understood as meaning the formation of doped zinc oxide by flame oxidation and flame hydrolysis. According to the invention, flame oxidation is to be understood as meaning the oxidation of zinc to zinc oxide in the gas phase in a flame produced by the reaction of a combustion gas, preferably hydrogen, and oxygen. According to the invention, flame hydrolysis is to be understood as meaning the hydrolysis and subsequent oxidation of the doping agents in the same flame.

In that process, highly disperse, non-porous primary particles are first formed, which grow together to form aggregates as the reaction progresses, and those aggregates may join together further to form agglomerates.

Doping component is to be understood as meaning one or more oxides of the above-mentioned metals, as are present in the powder according to the invention. Doping agent is to be understood as meaning a substance which carries an above-mentioned metal as metal component and which is converted into the oxide during the preparation of the powder according to the invention. The content of doping component in the zinc oxide powder according to the invention is based on the particular oxide in question.

The primary particles are to be understood as being, in high-resolution TEM images, the smallest particles which obviously cannot be broken down further. Several primary particles can join together at their points of contact to form aggregates. Such aggregates are either difficult to separate again by means of dispersing devices or cannot be separated at all. Several aggregates can join together loosely to form agglomerates, it being possible for that process to be reversed again by suitable dispersion.

The mean maximum aggregate diameter is determined by image analysis following ASTM 3849-89. In that process, the maximum diameter of about 1500 aggregates is determined and the arithmetic mean is calculated therefrom. The maximum mean diameter describes the structure of an aggregate more accurately than the mean diameter.

The mean maximum aggregate diameter of the zinc oxide powder according to the invention may preferably have a value of from 50 to 300 nm and particularly preferably from 80 to 200 nm. Within those ranges, the electrical conductivity and the transparency have particularly advantageous values.

The aggregates of the powder according to the invention preferably have a largely anistropic structure, defined by a form factor F (circle) of less than 0.5. The parameter F (circle) describes the deviation of an aggregate from an ideal circular form. F (circle) is equal to 1 for an ideal circular object. The smaller the value, the further the structure of the object from the ideal circular form. The definition of the parameter is in accordance with ASTM 3849-89.

The mean primary particle diameter of the zinc oxide powder according to the invention, likewise determined from image analysis in accordance with ASTM 3849-89, may advantageously be from 5 to 30 nm.

The BET surface area of the zinc oxide powder according to the invention, determined in accordance with DIN 66131, may vary within wide limits, from 5 to 100 $m^2/g$. Values of from 30 to 70 $m^2/g$ are preferred.

The resistivity of the zinc oxide powder may also vary over a wide range. For applications in which zinc oxide is used in the form of an electrically conductive powder, it should be not more than $10^6$ Ohm×cm. It is preferably from $10^2$ to $10^4$ Ohm×cm, at a compressed density of 1.0 $g/cm^3$.

In addition, the transmission of the zinc oxide powder may have a value of more than 70%. That may be of importance for applications in which high transparency is required.

The amount of doping component in the zinc oxide powder according to the invention varies from 0.005 to 15 wt. % zinc oxide powder. The doping may preferably be from 0.1 to 6.0 wt. %. The range from 0.5 to 3.0 wt. % is particularly preferred.

A preferred doping component may be aluminium oxide.

A further preferred doping component may be a mixture of indium oxide and tin oxide. The amount of indium oxide is preferably from 90 to 99 wt. %, based on the sum of indium oxide and tin oxide, in each case calculated as oxide.

The invention also provides a process for the preparation of the doped zinc oxide powder according to the invention, which process is characterised in that the powder is obtained in four successive zones, a vaporisation zone, a nucleation zone, an oxidation zone and a quenching zone, from zinc powder and at least one doping agent, wherein, in the vaporisation zone, zinc powder is vaporised in a flame of air and/or oxygen and a combustion gas, preferably hydrogen, with the proviso that the reaction parameters are so chosen that oxidation of the zinc does not occur, and wherein, in the nucleation zone, into which there passes the hot reaction mixture from the vaporisation zone, consisting of zinc vapour, water vapour as the reaction product of the flame reaction, and optionally excess combustion gas, is cooled to temperatures of from 500 to 900° C. or is cooled by means of an inert gas, and an aerosol containing at least one doping agent is fed in in an amount that corresponds to the desired amount of the doping agent in the zinc oxide powder, and wherein, in the oxidation zone, the mixture from the nucleation zone is oxidised with air and/or oxygen, and wherein, in the quenching zone, the oxidation mixture is cooled to temperatures of less than 400° C. by the addition of cooling gas.

The aerosol may be obtained from aqueous, alcoholic and aqueous-alcoholic solutions or suspensions containing at least one doping agent.

Where more than one doping agent is used, the aerosols may be produced and introduced into the nucleation zone together or separately. Production of the aerosols may be carried out, for example, by means of a binary nozzle or by ultrasonic atomisation.

The process according to the invention may also be carried out by supplying the doping agent or agents to the nucleation zone in vaporised form instead of in the form of aerosols. In that case, the doping agents can be vaporised in the same manner as zinc powder, that is to say in a flame of air and/or oxygen and a combustion gas, preferably hydrogen, with the proviso that the reaction parameters are so chosen that oxidation of the doping agent does not occur. The doping agents may be vaporised separately or together with the zinc powder.

The process according to the invention can be carried out by supplying air and/or oxygen and the combustion gas at one or more locations within the vaporisation zone. Likewise, air and/or oxygen and the combustion gas can be supplied at one or more locations within the oxidation zone.

Separation of the zinc oxide powder from the gas stream may be carried out by means of filters, cyclone, washer or other suitable separators.

Figure 1B:
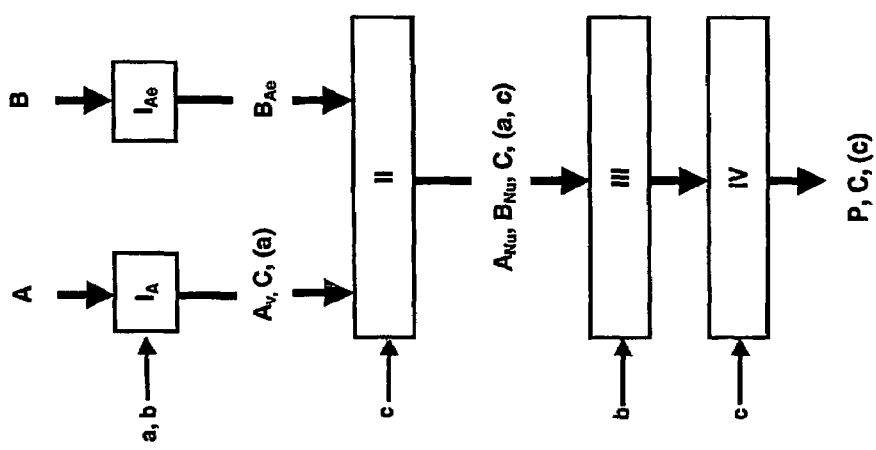

FIG. 1a-b show a simplified reaction scheme. In the figures:

A=zinc powder, $A_v$=zinc vapour, $A_{Nu}$=zinc particles in the nucleation zone, B=doping agent, $B_v$=vaporised doping agent, $B_{Nu}$=doping agent in the nucleation zone, $B_{Ae}$=doping agent in aerosol form C=water, P=doped zinc oxide powder, a=combustion gas, b=air and/or oxygen, c=inert gas (cooling gas), $I_A$=zinc powder vaporisation, $I_B$=doping agent vaporisation, $I_{A+B}$=vaporisation of zinc powder and doping agent together, $I_{Ae}$=conversion of doping agent into aerosol II=nucleation, III=oxidation, IV=quenching.

FIG. 1a shows a variant in which the zinc powder is vaporised and the doping agent is introduced into the nucleation zone in the form of an aerosol. FIG. 1b shows a variant in which zinc powder and the doping agent are vaporised together.

During the vaporisation of the zinc powder and optionally also of the doping agents, it is possible to use an excess of combustion gas, expressed in lambda values of from 0.5 to 0.99, preferably from 0.8 to 0.95.

It may also be advantageous for the temperature in the nucleation zone to be from 700° C. to 800° C.

Further variable process parameters are, for example, the rate of cooling and the dwell time in the individual stages of the process.

The rate of cooling in the nucleation zone is preferably from 100 K/s to 10,000 K/s, with values from 2000 K/s to 3000 K/s being particularly preferred. The rate of cooling in the quenching zone is preferably from 1000 K/s to 50,000 K/s, with values from 5000 K/s to 15,000 K/s being particularly preferred.

The dwell time in the vaporisation zone is preferably from 0.1 s to 4 s, with values from 0.5 s to 2 s being particularly preferred. The dwell time in the nucleation zone is preferably from 0.05 s to 1.00 s, particularly preferably from 0.1 s to 0.2 s. The dwell time in the oxidation zone is preferably from 5 ms to 200 ms, with values from 10 ms to 30 ms being particularly preferred. The dwell time in the quenching zone is preferably from 0.05 s to 1.00 s, with values from 0.1 s to 0.2 s being particularly preferred.

Halides, nitrates, alkyls, alkoxides and/or mixtures thereof may be used as doping agents. Particular preference is given to the use of the halides of aluminum, indium and tin.

The zinc oxide powder according to the invention can be used in electrically conductive, optionally transparent lacquers and coatings, as a filler or in sun protection formulations.

The doped zinc oxide powder according to the invention acquires its properties, such as, for example, a defined aggregate size, electrical conductivity, or transparency, owing to the novel preparation process. Compared with the prior art, where pyrogenic processes always start with the oxidation of the vapour of zinc and doping agent, the zinc vapour in the process according to the invention is cooled below the boiling point of the zinc prior to the oxidation. As a result, nucleation with the formation of zinc crystallites is able to occur. The doping agent is added to that nucleation zone.

The mechanism of that formation and the structure of the crystallites has not been clarified. By varying the process parameters, such as, for example, rates of cooling, dwell times and/or temperatures, it is possible to adapt the properties of the powder to the particular requirements.

EXAMPLES

Analytical Methods

The BET surface area is determined in accordance with DIN 66131.

The TEM images are obtained using a Hitachi TEM device, type H-75000-2. Approximately from 500 to 600 aggregates are evaluated by means of the CCD camera of the TEM device and subsequent image analysis.

The parameter F (shape) is equal to the quotient of the minimum aggregate diameter to the maximum aggregate diameter. The parameter F (circle) is calculated as follows: F (circle)=4Π×mean surface area)/2(P), where P=circumference of the aggregates.

The parameters F (shape) and F (circle) describe the deviation of a particle from an ideal circular shape. F (shape) and F (circle) are 1 for an ideal circular object. The smaller the value, the more removed the structure of the object from the ideal circular shape. The parameters are defined in accordance with ASTM3849-89.

Transmission

The transmission of the powders is determined in a dispersion which contains 1 wt. % powder and 99 wt. % water and is dispersed first by means of a dissolver (2000 rpm, 5 min) and then by means of an ultrasonic finger (amplitude 80%, 4 min). 2.0 g of the dispersion are removed and made up to 100 g with water. The transmission and scattered light for that dispersion are determined using a turbidimeter (Hach, 2100AN turbidimeter).

Resistivity

The resistivity of the powders is measured at room temperature and 40% relative humidity as a function of the compressed density (0.0–1.6 g/cm$^3$). To that end, the specimen is placed between two movable electrodes, and the current flow is determined after application of a direct current. The density of the powder is then increased stepwise by reducing the distance between the electrodes, and the resistance is measured again. The measurement is carried out following DIN IEC 93.

Example 1

Zinc powder (1000 g/h, particle size $\leq$5 μm) is transferred by means of a nitrogen stream (2.5 m$^3$/h) into a vaporisation zone in which a hydrogen/air flame (hydrogen: 4.78 m$^3$/h, air: 10.30 m$^3$/h, lambda=0.9) is burning. The zinc powder is vaporized thereby. The reaction mixture of zinc vapour, hydrogen, nitrogen and water is then cooled to a temperature of 850° C. by the metering in of 2 m$^3$/h of nitrogen, and 300 g/h of a 10 wt. % aqueous aluminium chloride solution (AlCl$_3$×6 H$_2$O) are fed in in the form of an aerosol. 3 m$^3$/h of oxidising air and 20 m$^3$/h of quenching gas are then added, whereupon the reaction temperature falls to values of about 530° C. The doped zinc oxide powder is separated from the gas stream by filtration.

Example 2

Zinc powder (1000 g/h, particle size $\leq$5 μm) is transferred by means of a nitrogen stream (2.5 m$^3$/h) into a vaporisation zone in which a hydrogen/air flame (hydrogen: 4.53 m$^3$/h, air: 9.68 m$^3$/h, lambda=0.9) is burning. The zinc powder is vaporised thereby. The reaction mixture of zinc vapour, hydrogen, nitrogen and water is then cooled to a temperature of 870° C. by the metering in of 2 m$^3$/h of nitrogen, and 350 g/h of a 5 wt. % aqueous indium (III) chloride solution (InCl$_3$×4 H$_2$O) are fed in in the form of an aerosol. 3 m$^3$/h of oxidising air and 20 m$^3$/h of quenching gas are then added, whereupon the reaction temperature falls to values of about 680° C. The doped zinc oxide powder is separated from the gas stream by filtration.

Example 3

Zinc powder (950 g/h, particle size $\leq$5 μm) is transferred by means of a nitrogen stream (2.5 m$^3$/h) into a vaporisation zone in which a hydrogen/air flame (hydrogen: 4.53 m$^3$/h, air: 9.68 m$^3$/h, lambda=0.9) is burning. The zinc powder is vaporised thereby. The reaction mixture of zinc vapour, hydrogen, nitrogen and water is then cooled to a temperature of 880° C. by the metering in of 2.5 m$^3$/h of nitrogen, and 320 g/h of a 6 wt. % aqueous solution of a 95:5 mixture (based on the respective oxides) of indium (III) chloride (InCl$_3$×4 H$_2$O) and tin tetrachloride (SnCl$_4$) are fed in in the form of an aerosol. 3 m$^3$/h of oxidising air and 20 m$^3$/h of quenching gas are then added, whereupon the reaction temperature falls to values of about 650° C. The doped zinc oxide powder is separated from the gas stream by filtration.

Example 4 (Comparison Example)

Zinc powder (200 g/h, particle size $\leq$5 μm) and 14.3 g/h of aluminium chloride are transferred by means of a nitrogen stream (1.5 m$^3$/h) into a vaporisation zone in which a hydrogen/air flame (hydrogen: 5 m$^3$/h, air: 23 m$^3$/h, lambda =1.93) is burning. The reaction mixture of zinc vapour, doping agent, hydrogen, nitrogen and water is then cooled to a temperature of 990° C. by the metering in of 1.5 m$^3$/h of nitrogen. 5 m$^3$/h of oxidising air and 15 m$^3$/h of quenching gas are then added, whereupon the reaction temperature falls to values of about 440° C. The doped zinc oxide powder is separated from the gas stream by filtration.

Example 5 (Comparison Example)

Zinc powder (300 g/h, particle size $\leq$5 μm) is transferred by means of a nitrogen stream (1.5 m$^3$/h) into a vaporisation zone in which a hydrogen/air flame (hydrogen: 4.6 m$^3$/h, air: 9.0 m$^3$/h, lambda=0.84) is burning. The zinc powder is vaporised thereby. The reaction mixture of zinc vapour, hydrogen, nitrogen and water is then cooled to a temperature of 870° C. by the metering in of 1.5 m$^3$/h of nitrogen. 4 m$^3$/h of oxidising air and 30 m$^3$/h of quenching gas are then added, whereupon the reaction temperature falls to values of about 300° C. The doped zinc oxide powder is separated from the gas stream by filtration.

The process parameters for the tests are shown in Table 1, and the product properties of the resulting powders are shown in Table 2.

The powders of Examples 1 and 3 prepared by the process according to the invention have a mean maximum aggregate diameter of approximately from 110 to 150 nm. Very good values for the transmission and resistivity are obtained. The powder of Comparison Example 4, in which the oxidation takes place above the boiling temperature of the zinc powder, has a mean maximum aggregate diameter markedly higher than 300 nm. The resulting values for transmission and resistivity are markedly above those of the powders according to the invention of Examples 1 to 3. Example 5 describes the preparation of an undoped zinc oxide powder, which is obtained by oxidation below the boiling temperature of zinc. The transmission of that powder is comparable with that of the powders according to the invention, but its resistivity is markedly higher.

TABLE 1

Process parameters

|  |  |  | Example 1 | Example 2 | Example 3 | Example 4 | Example 5 |
|---|---|---|---|---|---|---|---|
| Vaporisation | Zinc | g/h | 1000 | 1000 | 950 | 200 + 14.3 [(1)] | 300 |
|  | Nitrogen | m³/h | 2.5 | 2.5 | 2.5 | 1.5 | 1.5 |
|  | Hydrogen | m³/h | 4.78 | 4.53 | 4.53 | 5 | 4.6 |
|  | Air | m³/h | 10.3 | 9.68 | 9.68 | 23 | 9.0 |
|  | Lambda |  | 0.9 | 0.9 | 0.9 | 1.93 | 0.84 |
| Nucleation | Doping agent |  |  | $InCl_3 \times 4H_2O$ | $InCl_3 \times 4H_2O$ + $SnCl_4$ [(2)] | $AlCl_3 \times 6H_2O$ | — |
|  | Amount of doping agent | g/h | 300 g/h (10% sol.) | 350 g/h (5% sol.) | 320 g/h (6% sol.) | — | — |
|  | Cooling gas | m³/h | 2 | 2 | 2.5 | 1.5 | 1.5 |
|  | Temperature | °C. | 850 | 870 | 880 | 990 | 870 |
| Oxidation | Oxidising air | m³/h | 3 | 3 | 3 | 5 | 4 |
| Quenching | Quenching gas | m³/h | 20 | 20 | 20 | 15 | 30 |
|  | Temperature | °C. | ca. 530 | ca. 680 | ca. 650 | ca. 440 | ca. 296 |

[(1)] Zinc (200 g/h) and aluminium chloride (14.3 g/h) are vaporised together;
[(2)] Ratio: 95:5 (based on oxides)

TABLE 2

Product properties

|  |  | Example 1 | Example 2 | Example 3 | Example 4 | Example 5 |
|---|---|---|---|---|---|---|
| Doping |  | Aluminium oxide | Indium oxide | Indium oxide/ tin oxide | Aluminium oxide | — |
| Doping amount | wt. % | 2.0 | 2.6 | 2.8/0.15 | 3.0 | — |
| Mean maximum aggregate diameter | nm | 109 | 145 | 130 | 1374 | 133 |
| Form factor F(circle) |  | 0.41 | 0.41 | 0.41 | n.d. [(1)] | 0.32 |
| Form factor F(shape) |  | 0.64 | 0.63 | 0.62 | n.d | 0.61 |
| Mean aggregate surface area | nm² | 4734 | 8666 | 7243 | n.d. | n.d. |
| Mean primary particle diameter | nm | 23 | 20 | 19 | n.d. | n.d. |
| BET surface area | m²/g | 20 | 23 | 25 | 8.3 | 20 |
| Resistivity | Ω × cm | $10^2$ | $10^5$ | $10^3$ | $4.3 \times 10^9$ | $10^8$ |
| Transmission | % | 71.2 | 83.8 | 83.8 | n.d. | 72.7 |

[(1)] n.d. = not determined

The invention claimed is:

1. A pyrogenically prepared, doped zinc oxide powder, comprising a doping component, which comprises at least one oxide selected from the group consisting of aluminum oxides, gallium oxides, indium oxides, germanium oxides, tin oxides, and silicon oxides,
   and wherein the doped zinc oxide powder is in the form of aggregates having a mean maximum diameter of from 30 to 400 nm,
   and wherein the doping component is present in an amount from 0.005 to 15 wt. %.

2. The zinc oxide powder according to claim 1, wherein the mean maximum aggregate diameter has a value of 50 to 300 nm.

3. The zinc oxide powder according to claim 1, wherein the aggregates have a largely anisotropic structure defined by a form factor F(circle) of less than 0.5.

4. The zinc oxide powder according to claim 1, wherein the mean primary particle diameter is from 5 to 30 nm.

5. The zinc oxide powder according to claim 1, wherein the BET surface area is from 5 to 100 m²/g.

6. The zinc oxide powder according to claim 1, wherein said powder has a resistivity of not more than $10^5$ Ohm×cm.

7. The zinc oxide powder according to claim 1, wherein said powder has a transmission of at least 70%.

8. The zinc oxide powder according to claim 1, wherein the amount of the doping component is from 0.2 to 6.0 wt. %.

9. The zinc oxide powder according to claim 1, wherein the doping component is aluminum oxide.

10. The zinc oxide powder according to claim 1, wherein the doping component is a mixture of indium oxide and tin oxide.

11. A process for the preparation of zinc oxide powder, the process comprising
   preparing, from zinc powder and at least one doping agent, the zinc oxide powder of claim 1,
   wherein the preparing is in four successive zones, which are a vaporization zone, a nucleation zone, an oxidation zone and a quenching zone,
   and wherein, in the vaporization zone, zinc powder is vaporized in a flame of air and/or oxygen and a combustion gas, to form a hot reaction mixture, with the proviso that the reaction parameters are so chosen that oxidation of the zinc does not occur,
   and wherein, in the nucleation zone, into which there passes the hot reaction mixture from the vaporization zone, comprising zinc vapour, water vapour as the reaction product of the flame reaction, and optionally excess combustion gas, said mixture is cooled to temperatures from 500 to 900° C. or is cooled by means of an inert gas, and wherein, at least one doping agent in vaporized form, or an aerosol containing at least one doping agent, is fed in in an amount that corresponds to the desired amount of the doping agent in the zinc oxide powder, to form a mixture, and wherein, in the oxidation zone, the mixture from the nucleation zone is oxidized with air and/or oxygen, to form an oxidation mixture, and wherein, in the quenching zone, the oxidation mixture is cooled to temperatures less than 400° C., by the addition of cooling gas.

12. The process according to claim 11, wherein there is fed to the nucleation zone, instead of the aerosol, the at least one doping agent in vaporized form.

13. The process according to claim 11, wherein an excess of combustion gas, expressed in lambda values from 0.5 to 0.99, is used in the vaporization of zinc powder and the at least one doping agent.

14. The process according to claim 11, wherein the temperature in the nucleation zone is from 700° C. to 800° C.

15. The process according to claim 11, wherein the rate of cooling is from 100 K/s to 10,000 K/s in the nucleation zone, and from 1000 K/s to 50,000 K/s in the quenching zone.

16. The process according to claim 11, wherein the dwell time is from 0.1 s to 4 s in the vaporization zone, from 0.05 s to 1.00 s in the nucleation zone, from 0.05 s to 1.00 s in the quenching zone, and from 5 ms to 200 ms in the oxidation zone.

17. The process according to claim 11, wherein the at least one doping agent is selected from the group consisting of halides, nitrates, alkyls, alkoxides and mixtures thereof.

18. An electrically conductive, optionally transparent lacquer or coating, comprising the zinc oxide powder of claim 1, and one or more additives.

19. A filler, comprising the zinc oxide powder of claim 1, and one or more additives.

20. A sun protection formulation, comprising the zinc oxide powder of claim 1, and one or more additives.

* * * * *